Figure 1:
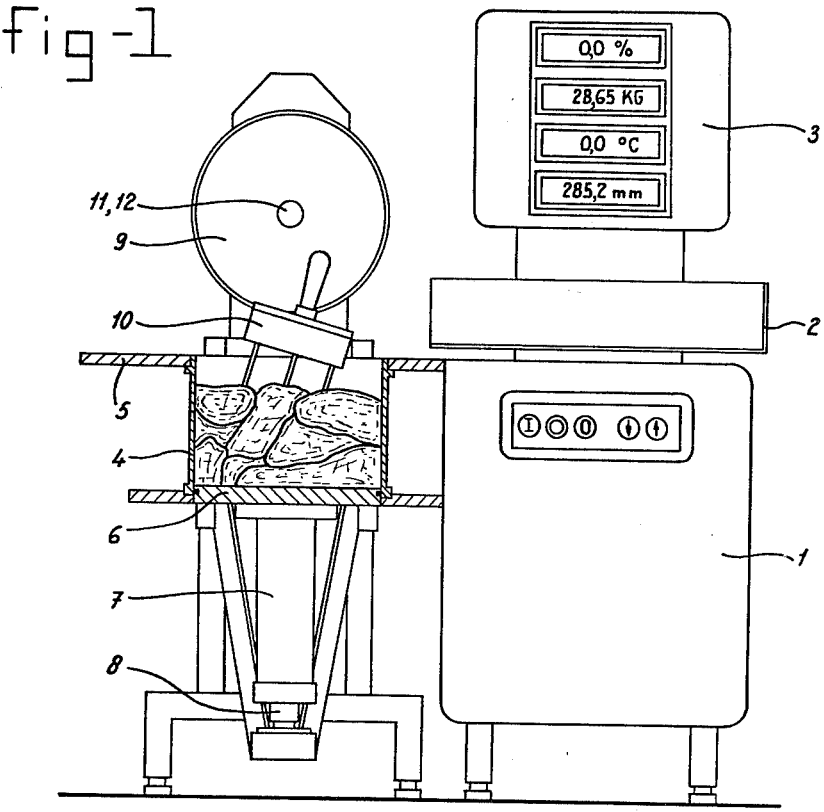

United States Patent [19]

van Haren

[11] 4,449,406
[45] May 22, 1984

[54] METHOD AND DEVICE FOR MEASURING THE FAT CONTENT OF MEAT

[75] Inventor: Lambertus F. W. van Haren, Druten, Netherlands

[73] Assignee: Protecon B.V., AG Oss, Netherlands

[21] Appl. No.: 348,055

[22] PCT Filed: Jun. 2, 1981

[86] PCT No.: PCT/NL81/00017
§ 371 Date: Jan. 29, 1982
§ 102(e) Date: Jan. 29, 1982

[87] PCT Pub. No.: WO81/03547
PCT Pub. Date: Dec. 10, 1981

[30] Foreign Application Priority Data
Jun. 2, 1980 [NL] Netherlands .................. 8003203

[51] Int. Cl.³ .............................................. G01N 9/02
[52] U.S. Cl. .................................. 73/433; 73/432 R
[58] Field of Search .......................... 73/432 Z, 433

[56] References Cited

U.S. PATENT DOCUMENTS 3,282,115 11/1966 Taylor .............................. 73/432 Z
3,417,625 12/1968 Whitehead ............................ 73/433
3,487,698 1/1970 Leger et al. .......................... 73/433

*Primary Examiner*—S. Clement Swisher
*Attorney, Agent, or Firm*—Harness, Dickey & Pierce

[57] ABSTRACT

For measuring the fat content of meat it is known to determine the specific gravity of the meat, which at a given temperature and for a given type of meat is a measure for the fat content. This invention provides a novel way to realize this easily and rapidly in the factory, e.g. in a production line. Thereto, meat portions are weighed and compressed in a closed space, of which the volume in compressed condition of the meat is determined, so that the ratio of weight and volume gives the specific gravity. The weighing device is mounted to the side of an upstanding cylinder press with its top at the level of the weighing surface or of an immediately adjacent table surface, an easily movable cover to open and close the cylinder and a bottom being a press platen piston movable up and down to compress the meat with closed cover and to move it further upwards to above the cylinder with open cover.

6 Claims, 2 Drawing Figures

U.S. Patent

May 22, 1984

4,449,406

METHOD AND DEVICE FOR MEASURING THE FAT CONTENT OF MEAT

The invention relates to a method for measuring the fat content of meat by determining the specific gravity and to a device for executing said method therewith.

The fat content of meat may be determined in different manners. It is possible to do this by measuring the transparency of the meat for X-rays, by measuring high frequency induction in the meat and by extraction and melting out methods. In part such methods are destructive, in part not. It is also known to determine the fat content of meat from the specific gravity thereof at a laboratory scale, in which for known meat type and temperature of the meat the weight of a determined volume of the meat is measured by submerging in water. This method is not suited for the frequent application to large quantities of meat in the factory, although the attractivity thereof is that it is not destructive.

The invention now aims at providing a new method and device allowing a rapid determination with only few requirements as to skil of personnel and extensive manual labour, so that in a production line without much delay a frequent determination is possible.

To this end a method as indicated in the preamble is according to the invention characterized in that one weighs a quantity of the meat, compresses it in a closed space, measures the volume in compressed condition and determines the fat content from the proportion of said weight to said volume.

A device for realising said method is according to the invention characterized in that it comprises a weighing device with a weighing table for taking up the meat, an upstanding cylinder positioned immediately to the side thereof, of which cylinder the upper edge does not protrude above the weighing table, a cover for easily closing and opening said cylinder in its upper surface and a bottom of said cylinder movable up and down and having driving means to operate as a press platen and indicating means for the position of said press platen in order to determine therefrom with the meat compressed the volume, which press platen is movable up and down into the plane of a table such as the weighing table, near the upper edge of the cylinder, in order to allow easy moving of the meat out of and/or into the cylinder.

It is thus not necessary to use an accurately metered quantity of meat and it is possible to use a simple piston press with indication of the position of the piston to determine the compressed volume directly. It would be possible to determine the weight of the meat in said press, but by the heavy piston with parts to move it this is not easily done accurately, so that it is preferred to measure outside the press. This for instance is possible by providing a weighing scale directly to the side of the press in fixed position, from which scale it is possible to slide the meat into the piston press with open top having an easily adaptable and removable lid in its top surface and having as a bottom the press platen movable up and down.

It is possible to measure the temperature of the meat on the weighing scale or in the open press space with a thermometer to be stabbed into the meat, for instance with a few feelers each with a thermo couple, and to determine the average of the measured temperatures, for instance automatically in said thermometer. A micro processor may process the measured weight, the measured volume and the measured temperature to give directly an indication of the specific gravity or of the fat content.

The temperature should be determined at 1° accurately, the weight for small portions of meat on 2 g accuracy ($\pm 1$ g), for bigger portions increasing to 10, i.e. $\pm 5$ g.

In order not to obtain an inaccuracy in measurement by air and other gases and vapours between and above the portions of meat it is preferred to put the meat under vacuum when measuring the volume, and when applying the above indicated method and device this is easily obtainable by providing the cover on the upstanding cylinder for pressing with a connection for vacuum, for instance with a valve kept open by spring action and adapted to be pushed to the closed position by the meat when compressing it by the upwardly moving piston, so that no meat can enter the suction duct.

Figure 2:
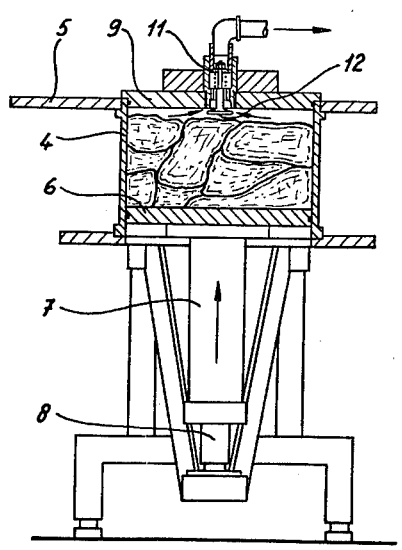

The invention will now be explained further with reference to the enclosed drawing. Therein:

FIG. 1 is a verticle section and view of a device according to the invention in a preferred embodiment, and FIG. 2 is a detail of the press cylinder thereof in closed condition.

A weighing device 1 has a scale 2, indicating means 3 to indicate weight, temperature, volume and fat content of the meat and a simple computer to calculate said fat content from the measured values. To the side of said weighing device 1 there is an upstanding measuring cylinder 4, opening at the top in a table surface 5, joining the weighing device 1.

A press piston 6 is movable fittingly up and down in the cylinder and is driven by a hydraulic or pneumatic jack 7, the piston 6 being rigidly connected to the cylinder of the jack 7, the piston rod 8 of the jack being stationarily mounted. This unity is provided with a measuring device for the position of the jack and thus of the press piston 6, formed for instance by a known electric length rule or electronic measuring rule of which one of the mutually slidable parts, for instance a magnet, moves with the cilinder of the jack 7. The measured position is indicated at 3.

A cover 9 is pivotally mounted behind the cylinder 4 and can easily be tipped down to close the cylinder hermetically.

In FIG. 1 it has been indicated in what way a thermometer 10, for instance with three measuring teeth each with a thermo couple, can be stabbed in the meat in cylinder 4 to measure the temperature thereof, which is transmitted by a signal line to the indicating means 3, so that the computer determines the average temperature therefrom, or it is possible for the thermometer itself to determine said average temperature.

The cover 9 has been shown in FIG. 2 in tipped down and closed position. It has a central connection 11 for a vacuum duct, with a valve 12 pushed by a spring to the lower open position. The cover has a lock which has not been shown in detail such as a known toggle to be maintained in the closed position.

Now one acts as follows. In a production line each time at desired intervals a portion of meat is put on the scale 2 of the weighing device and after weighing is slid into the open, now empty cylinder 4 to the side thereof, of which the press piston 6 is in the lower position. After measuring with thermometer 10 the cover 9 is closed (FIG. 2), vacuum is connected to the cylinder and through connection 11 and the press piston 6 is moved upwardly. The meat will therewith eventually push valve 12 to close it and prevents that meat or liquid parts enter said connection. The press piston 6 is moved upwardly until the pressure in the cylinder has increased to for instance ±10 bar. The indicating means 3 now show the position of the press piston 6 and the computer is fed with the indication thereof, which, while taking into account the measured temperature, determines therefrom and from the measured weight the fat content, which is also indicated by said means 3 and if desired may be recorded automatically.

Now the vacuum is interrupted, the cover 9 is opened, the piston 6 is moved upwardly further until the top surface thereof is positioned at the height of table surface 5 and the meat is slid away over said table.

It is thus possible to determine the fat content of portions of meat in the factory very rapidly and accurately.

I claim:

1. A method for measuring the fat content of meat by determining the specific gravity comprising the steps of first weighing a quantity of meat outside a device to compress it, the compression device comprising an upstanding cylinder open at its top with a bottom movable up and down, subsequently placing the weighted quantity of meat in, closing said cylinder from above when the meat is placed in it, compressing the weighed quantity in the closed space by moving the bottom upwardly until the meat in the cylinder is under a certain compression, and measuring the compressed volume in the compressed condition by determining the position of the movable bottom and determining the fat content from the portion of said weight to said volume, and opening the cylinder at its top after the compression and moving the movable bottom upwardly further to remove the meat from the cylinder.

2. A method for measuring the fat content of meat by dettermining the specific gravity comprising the steps of weighing a quantity of the meat, placing the weighed quantity of meat in a closed space, compressing the weighed quantity in the closed space, reducing the pressure in said closed space during the compressing of the meat and measuring the compressed volume in the compressed condition and determining the fat content from the portion of said weight to said volume.

3. Method according to claim 2, characterized in that the meat is weighed outside a device to compress it, the compression device comprising an upstanding cylinder open at its top with a bottom movable up and down, closing said cylinder from above when the meat is placed in it, moving the bottom upwardly until the meat in the cylinder is under a certain compression, determining the volume from the position of the movable bottom therewith, opening the cylinder at its top after the compression and moving the movable bottom upwardly further to remove the meat from the cylinder.

4. Device for measuring the fat content of meat by determining the specific gravity thereof comprising a weighing device with a weighing table for weighing a mass of the meat, an upstanding cylinder positioned immediately to the side of said weighing table, of which the upper edge does not protrude above said weighing table, a cover to close and open this cylinder at its top surface and a bottom of said cylinder movable up and down, driving means to operate said bottom as a press platen and indicating means for the position of said press platen in order to determine the volume therefrom with the meat in compressed condition, said press platen being movable upwardly into the plane of a table such as the weighing table near the upper edge of the cylinder to allow easy movement of the meat over said edge out of/or into the cylinder.

5. Device for measuring the fat content of meat by determining the specific gravity thereof comprising a weighing device with a weighing table for weighing a mass of the meat, an upstanding cylinder positioned immediately to the side of said weighing table, of which the upper edge does not protrude above said weighing table, a cover to close and open this cylinder at its top surface, said cover of the cylinder having a connection in order to exert a reduced pressure in the cylinder and a bottom of said cylinder movable up and down, driving means to operate said bottom as a press platen and indicating means for the position of said press platen in order to determine the volume therefrom with the meat in compressed condition, said press platen being movable upwardly into the plane of a table such as the weighing table near the upper edge of the cylinder to allow easy movement of the meat over said edge out of/or into the cylinder.

6. Device according to claim 5, characterized in that said connection in said cover has a valve opening towards the space within the cylinder, which is pushed to the closed position by the meat moving upwardly during pressing.

* * * * *